(12) United States Patent
Bryant et al.

(10) Patent No.: US 7,258,684 B2
(45) Date of Patent: Aug. 21, 2007

(54) SYSTEM AND METHOD FOR DISGUISING PERSONAL CARE PRODUCTS

(75) Inventors: Kristi Bryant, Appleton, WI (US); Glory Alcantara, Neenah, WI (US); Mary L. McDaniel, Appleton, WI (US); Michelle Sroda, Greenbay, WI (US); Susan Weyenberg, Appleton, WI (US); Katherine C. Wheeler, Menasha, WI (US); Teresa Zander, Bonduel, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 383 days.

(21) Appl. No.: 10/705,738

(22) Filed: Nov. 11, 2003

(65) Prior Publication Data

US 2005/0101931 A1   May 12, 2005

(51) Int. Cl.
*A61F 13/15* (2006.01)
*A41B 9/00* (2006.01)
*A41B 9/06* (2006.01)

(52) U.S. Cl. .............................. 604/396; 2/109; 2/113; 604/393; 604/394; 604/402

(58) Field of Classification Search ................ 604/367, 604/385.01, 393–396, 400–402; 2/78.1, 2/109, 111, 406–408
See application file for complete search history.

(56) References Cited

U.S. PATENT DOCUMENTS

| 4,446,572 | A | 5/1984 | Lindquist |
| 5,591,147 | A | 1/1997 | Couture-Dorschner et al. |
| 5,612,118 | A | 3/1997 | Schleinz et al. |
| 5,993,431 | A | 11/1999 | McFall et al. |
| 6,140,551 | A | 10/2000 | Neimeyer et al. |
| 6,231,715 | B1 | 5/2001 | Schleinz et al. |
| 6,277,105 | B1 | 8/2001 | Rynish |
| 6,558,499 | B1* | 5/2003 | Pargass et al. ............... 156/250 |
| 6,569,136 | B1 | 5/2003 | Tao et al. |
| 6,710,221 | B1* | 3/2004 | Pierce et al. ................. 604/361 |
| 2003/0187415 | A1* | 10/2003 | Kudo et al. .................. 604/367 |
| 2005/0054253 | A1* | 3/2005 | Minoguchi et al. .......... 442/327 |
| 2005/0124955 | A1* | 6/2005 | Adams et al. .......... 604/385.01 |
| 2005/0154365 | A1* | 7/2005 | Zander et al. .......... 604/385.04 |

FOREIGN PATENT DOCUMENTS

| EP | 0286543 A2 | 10/1988 |
| EP | 1138293 A1 | 10/2001 |
| EP | 1179329 | 2/2002 |
| EP | 1327427 | 7/2003 |
| WO | WO 0038915 A1 | 7/2000 |
| WO | WO 0121126 A1 | 3/2001 |
| WO | WO 0230347 A1 | 4/2002 |
| WO | WO 02083047 A1 | 10/2002 |
| WO | WO 03013406 A1 | 2/2003 |
| WO | WO 03013409 A1 | 2/2003 |
| WO | WO 03068123 A2 | 8/2003 |

* cited by examiner

*Primary Examiner*—Tatyana Zalukaeva
*Assistant Examiner*—Melanie J Hand
(74) *Attorney, Agent, or Firm*—Dority & Manning, P.A.

(57) ABSTRACT

The present invention discloses and claims a system and method for disguising a personal care product. The personal care product includes a pattern that matches a design on an undergarment so that the personal care product blends into the background of the undergarment. The method for disguising the personal care product includes creating a pattern to match the design on the undergarment and placing the pattern on the personal care product.

29 Claims, 5 Drawing Sheets

SYSTEM AND METHOD FOR DISGUISING PERSONAL CARE PRODUCTS

BACKGROUND OF THE INVENTION

Personal care products are designed to intercept and capture body exudates, such as urine and menses. Examples of commonly available personal care products include adult care products, such as incontinence pants and pads; child care products, such as diapers and training pants; and feminine care products, such as sanitary pads, panty liners, inter-labial absorbent articles, and tampons. A user wears the product either in place of an undergarment, as with child care products and some adult care products, or beneath the undergarment, as with feminine care products and other adult care products. The user generally wears the personal care product a single time and discards the product after a relatively short period of use.

By their nature, personal care products are individual and private items. Consumers prefer products that are comfortable, inconspicuous, and invisible from outside of the undergarment or clothing. Ideally, the personal care product should fully cover the user's pudendum and possess sufficient fluid capacity, yet remain essentially non-visible from the outside of the undergarment. In practice, fully covering the user's pudendum and possessing sufficient fluid capacity may result in an absorbent article that is less comfortable, more conspicuous, and more visible from the outside of the undergarment.

Historically, personal care products have been white and non-descript. This appearance conveyed a sense of a clean, hygienic, and sanitary product. In addition, the white, non-descript color permitted the personal care product to blend easily with undergarments that were also predominantly white. Currently, however, fashion trends have moved in the direction of colored and printed undergarments in a variety of styles. As a result, white, non-descript personal care products now tend to be more conspicuous and more visible when worn with colored and printed undergarments.

In addition, many consumers infer various characteristics of a personal care product based solely on the appearance of the product. For example, consumers may associate plain, white, non-descript products as being less comfortable, cheaper, and of lower quality than identical products having a contemporary, aesthetic design, print, or color. This is especially true when the white, non-descript products are sold directly next to substantially identical products having a contemporary, aesthetic design, print, or color.

Experience has shown that the look and feel of personal care products can also create or increase apprehension among users. For example, people suffering from incontinence often wear absorbent diapers or pads in lieu of or beneath their undergarments to capture and retain body exudates. The absorbent articles tend to look and feel slightly different than the user's normal undergarment. This difference in look and feel creates a constant reminder to the user of the incontinence problem, thus creating a constant source of apprehension with the user.

Many conventional personal care products include side flaps, wings, or tabs to help reduce leakage by providing additional lateral coverage to the crotch of the undergarment. The side flaps, wings, or tabs extend beyond the undergarment, making these extensions more visible and conspicuous. Some manufacturers have made the extensions transparent or translucent in an effort to reduce the visibility and conspicuousness of the extensions. However, transparent or translucent materials tend to be stiff, shiny, and lack absorbency. As a result, transparent or translucent extensions tend to be less comfortable, just as visible and conspicuous, and lack the desirable absorbent capacity.

Therefore, a need exists for an improved personal care product that looks and feels like a typical undergarment. Moreover, a need exists for an improved personal care product that mimics the current colors, prints, and styles of undergarments. Lastly, a need exists for an improved personal care product having extensions that remain comfortable, inconspicuous, and absorbent.

SUMMARY OF THE INVENTION

Objects and advantages of the invention are set forth below in the following description, or may be obvious from the description, or may be learned through practice of the invention.

The present invention relates to a system for disguising the use of a personal care product. The system generally includes an undergarment, a personal care product designed to be placed at least partially within the undergarment, and a pattern defined on the personal care product to match the undergarment. The undergarment has a design of outwardly visible characteristics of any combination of non-white colors, shapes, and designs. The personal care product includes an absorbent material within an exterior layer that includes a top sheet and a back sheet. The pattern is defined on at least one of the top sheet and back sheet so that when the personal care product is placed in the undergarment, the pattern substantially matches the design on the undergarment and disguises the visible lines of distinction between the personal care product and the undergarment.

The pattern may be defined on the personal care product using any conventional technique, including printing or embossing, on either side of the exterior layer. Depending on the embodiment, the pattern may be any combination of geometric shapes, non-geometric shapes, repeating shapes, and non-repeating shapes. In addition, the pattern may be defined on all or only a part of the top sheet, back sheet, or a combination of the two. In a particular embodiment, the absorbent material includes laterally extending wings that fold around a crotch region of the undergarment, and the pattern is defined on the wings. In another particular embodiment, the top sheet includes a longitudinal strip with the pattern defined along opposite lateral sides of the longitudinal strip.

The present invention also includes a method for disguising the use of personal care products placed in a user's undergarment. The method includes selecting an undergarment having a design of outwardly visible characteristics of any combination of non-white colors, shapes, and designs; defining a pattern that substantially matches the visible design of the undergarment on at least one outwardly visible surface of a personal care product intended to be placed within the undergarment; and placing the personal care product in the undergarment such that the pattern substantially aligns with and matches the undergarment design. This method disguises the visible lines of distinction between the personal care product and the undergarment.

The method may also include defining the pattern on surfaces of the personal care product that are visible to the user in use of the personal care product. Alternately, the method may include defining the pattern on surfaces of the personal care product that are outwardly visible when the undergarment and personal care product are worn by the user. Particular embodiments may define the pattern substantially over a top sheet, a back sheet, or a combination of a top sheet and a back sheet. Moreover, the pattern may be defined on the personal care product by embossing or printing.

The present invention also includes a personal care product that is placed in an undergarment that has a design of outwardly visible characteristics of any combination of non-white colors, shapes, and designs. The personal care product includes an exterior layer with a pattern defined on at least a portion of the exterior layer. The exterior layer includes a top sheet and a back sheet. The pattern substantially matches the undergarment design to disguise visible lines of distinction between the personal care product and the undergarment.

The pattern may include any combination of geometric shapes, non-geometric shapes, repeating shapes, and non-repeating shapes. Furthermore, the pattern may be printed or embossed on part or substantially all of the top sheet, back sheet, or combination of the two.

Particular embodiments may include a top sheet having an un-patterned longitudinal strip with the pattern defined along opposite lateral sides of the longitudinal strip. In addition, the pattern may be on either side of the top sheet. An alternate embodiment may include laterally extending wings that fold around a crotch region of the undergarment with the pattern defined on the wings.

Those of ordinary skill in the art will better appreciate the features and aspects of such embodiments, and others, upon review of the specification.

BRIEF DESCRIPTION OF THE FIGURES

A full and enabling disclosure of the present invention, including the best mode thereof to one skilled in the art, is set forth more particularly in the remainder of the specification, including reference to the accompanying figures, in which.

DETAILED DESCRIPTION OF THE INVENTION

Reference will now be made in detail to present embodiments of the invention, one or more examples of which are illustrated in the accompanying drawings. Each example is provided by way of explanation of the invention, not limitation of the invention. In fact, it will be apparent to those skilled in the art that modifications and variations can be made in the present invention without departing from the scope or spirit thereof. For instance, features illustrated or described as part of one embodiment may be used on another embodiment to yield a still further embodiment. Thus, it is intended that the present invention covers such modifications and variations as come within the scope of the appended claims and their equivalents.

The present invention relates to a system and method for disguising a personal care product to match a design on an undergarment. Personal care products generally include adult care products, such as incontinence pants and pads; child care products, such as diapers and training pants; and feminine care products, such as sanitary pads, panty liners, inter-labial absorbent articles, and tampons. The accompanying figures depict the personal care product as a feminine care product, specifically a sanitary napkin having a conventional elongated oval shape. However, it should be understood by one of ordinary skill in the art that the accompanying figures merely provide an illustration of particular embodiments within the scope of the present invention without limiting the scope of the present invention or claims. As such, alternate embodiments within the scope of the present invention and claims may comprise adult care products, child care products, or other feminine care products. Furthermore, the personal care product may have other shapes, sizes, and thicknesses, depending on the particular application and embodiment.

Figure 1:
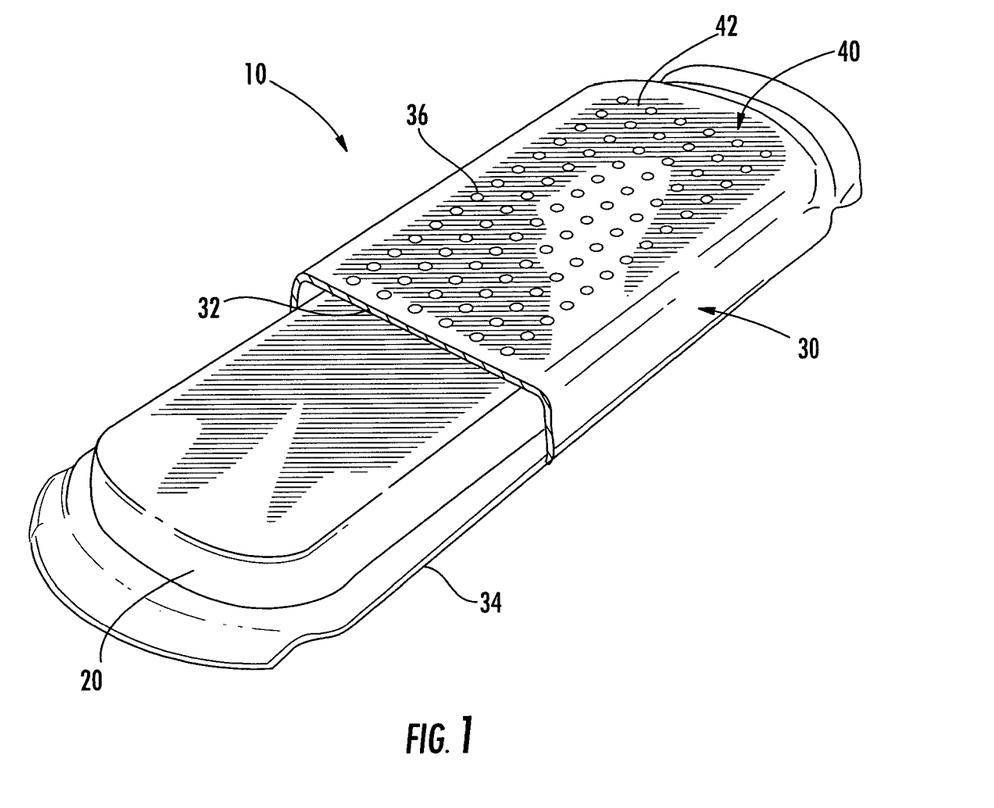
FIG. 1 is a perspective view of a partial cut-away of an embodiment of the present invention.
Figure 2A:
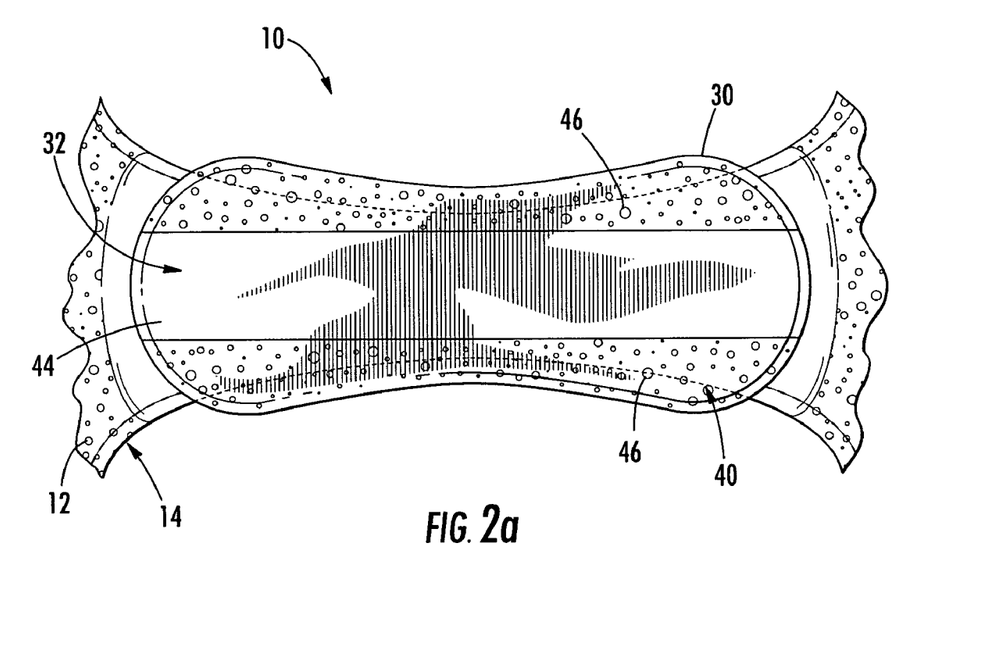
FIG. 2*a* is a top plan view of an embodiment of the present invention.
Figure 2B:
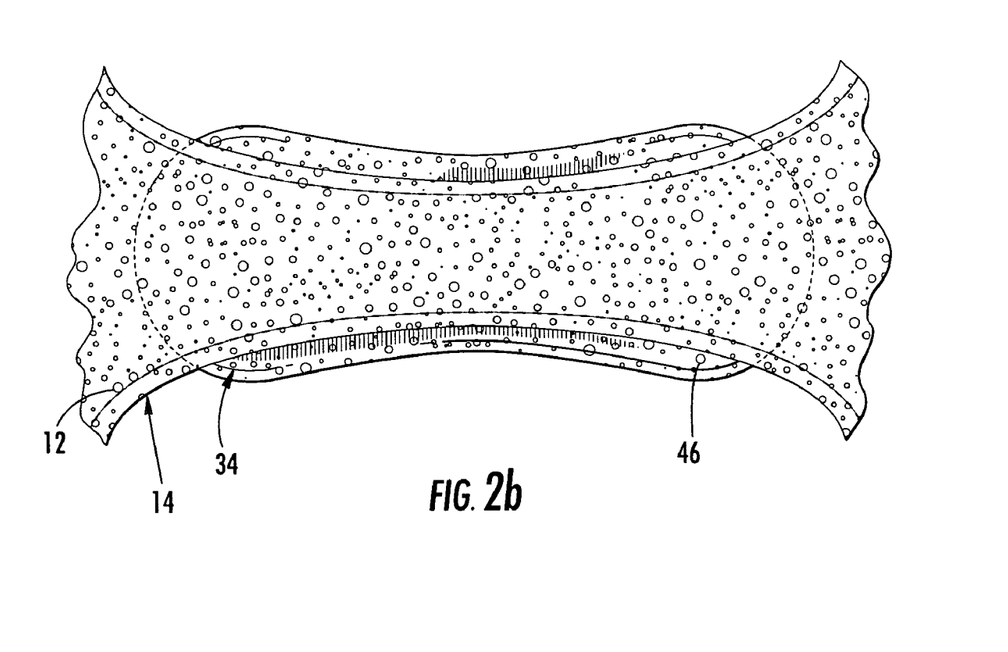
FIG. 2*b* is a bottom plan view of an embodiment of the present invention.

The personal care product 10 has a degree of absorbency for the intended use of the product. The absorbency may be provided by any one or combination of materials. Referring to FIGS. 1, 2*a*, and 2*b*, in a particular embodiment, the personal care product 10 generally includes an absorbent material 20, an exterior layer 30 covering the absorbent material 20, and a pattern 40 on the exterior layer 30. When properly positioned, body exudates pass through the exterior layer 30 for capture by the absorbent material 20. The pattern 40 disguises the personal care product 10 to match the design 12 on the undergarment 14 and/or convey a sense of quality and/or comfort to the user, as described in greater detail below.

The absorbent material 20 provides the operative material for collecting and retaining body fluids or exudates while remaining light and dry feeling during use. The absorbent material 20 should be soft, not stiff, and should retain its shape, even when wet. The absorbent material 20 may attach to portions of the exterior layer 30 to hold the absorbent material 20 in place and protect the absorbent material 20 from abrasion.

The absorbent material 20 may be any structure or combination of components which are generally compressible, conformable, non-irritating to the user's skin, and capable of absorbing and retaining bodily fluids. For example, the absorbent material 20 may include an absorbent web of cellulose fibers, such as wood pulp fibers, other natural fibers, synthetic fibers, woven or non-woven sheets, scrim netting or other stabilizing structures, superabsorbent materials, binder materials, surfactants, selected hydrophobic and hydrophilic materials, pigments, lotions, and odor control agents, as well as combinations thereof. In one embodiment, the absorbent material 20 is a matrix of cellulose fluff coated with superabsorbent hydrogel-forming particles. The absorbent material 20 may be formed using various methods and techniques known in the art, such as dry-forming, air forming, wet-forming, and foam-forming, as well as combinations thereof.

Superabsorbent materials are well known in the art and may be selected from natural, synthetic, and modified natural polymers and materials. The absorbent material 20 generally includes superabsorbent material, with the superabsorbent material ranging from about 0-90 percent by weight of the absorbent material 20, depending on the application and desired absorbency. For example, the total absorbency may be about 200-900 grams of 0.9% by weight saline for infant care products; whereas, the total absorbency for adult care products may be about 400-2000 grams of 0.9% by weight saline. For feminine care products, the total absorbency may be within the range of about 7-50 grams of menstrual fluid.

It should be appreciated that the separate layer of absorbent material 20 is not a requirement of the invention, and that absorbent capacity may be otherwise provided.

The exterior layer 30 provides a protective barrier for the absorbent material 20. The exterior layer 30 generally includes a liquid permeable top sheet 32 and a liquid impermeable back sheet 34, with each having an absorbent side and a non-absorbent side.

The top sheet 32 provides the personal care product 10 with a liquid permeable surface that contacts the user's skin. The top sheet 32 should provide a comfortable, conforming interface with the user's skin by being flexible, compliant, and non-irritating to the skin. The top sheet 32 should also transfer fluids quickly and remain dry and clean during use. In addition to being liquid permeable, the top sheet 32 may also include apertures 36 for freely passing exudates with minimal absorption. The top sheet 32 may be coated with a surfactant to further enhance permeability to the absorbent material 20 and reduce absorption by the top sheet 32. The top sheet 32 may be any woven or non-woven material which passes body fluids yet remains comfortable to the user. Examples of suitable top sheet materials include rayon, bonded carded webs of polyester, polypropylene, polyethylene, nylon, or other heat-bondable fibers, polyolefins, copolymers of polypropylene and polyethylene, linear low-density polyethylene, and aliphatic esters such as polylactic acid. A specific example of a suitable top sheet material is a bonded carded web made of polypropylene and polyethylene such as that used as cover stock for KOTEX® panty liners and obtainable from Sandier Corporation, Germany.

The back sheet 34 provides the personal care product 10 with a liquid impermeable and possibly vapor permeable surface. As such, the back sheet 34 prevents exudates from completely penetrating the personal care product 10 and soiling the user's undergarment 14 or outer clothing. Ideally, the back sheet 34 is soft, flexible, quiet, breathable, and may include some absorbent capacity on the side facing the absorbent material 20. The garment-facing side of the back sheet 34 may include adhesive strips or other suitable fastening device (not shown) for adhering the personal care product 10 to the user's undergarment 14. The back sheet 34 may be any suitable material known in the art, such as embossed and non-embossed thermoplastic films, laminated tissue, and polyethylene films. In one embodiment, the back sheet 34 includes a non-woven material laminated to a microporous film.

The pattern 40 on the exterior layer 30 provides several possible functions. As previously discussed in the Background of the Invention, users prefer personal care products that are inconspicuous, comfortable, and of high quality. The accompanying figures illustrate various embodiments of the present invention that incorporate a contemporary, aesthetic design, print, or color into the personal care product 10 to disguise the product 10 to match the design 12 on the undergarment 14 and/or convey a sense of comfort and/or quality to the user.

The pattern 40 may be as simple as a solid non-white color, such as black, natural, green, red, or pink. Other possible patterns 40 include repeating or random geometric shapes, flowers, paisley, or other figures. In this manner, the selected pattern 40 on the exterior layer 30 disguises the personal care product 10 to match or blend in with the design 12 of the undergarment 14. When placed in the undergarment, the pattern disguises any visible lines of distinction between the personal care product and the undergarment. As a result, the personal care product 10 is less visible from outside the undergarment 14 and less conspicuous to the user. In addition, the selected pattern 40 conveys a sense of comfort and/or quality to the user, especially when compared to a standard white product.

Referring again to FIG. 1, the pattern 40 on the personal care product 10 is a solid non-white color 42. The solid non-white color pattern 42 may provide the additional capability of concealing additives or exudates in the product 10. For example, a solid shade of green permits the manufacturer to add aloe or vitamin E to the top sheet 32 or absorbent material 20 without noticeably discoloring the exterior layer 30. Similarly, a solid shade of yellow, red, or brown may prevent exudates from noticeably discoloring the top sheet 32. Conversely, the manufacturer may select a solid color pattern 42 that noticeably discolors when exposed to exudates to indicate to the user that the product 10 is soiled and should be replaced.

FIGS. 2a and 2b provide top and bottom plan views, respectively, of an embodiment from inside and outside the undergarment 14. As shown in FIG. 2a, the top sheet 32 may include a longitudinal strip 44 with a random pattern 46 on opposite sides of the longitudinal strip 44. The random pattern 46 matches the design 12 on the undergarment 14 and disguises any visible lines of distinction between the personal care product and the undergarment. FIG. 2b illustrates the random pattern 46 on the back sheet 34. In this embodiment, the longitudinal strip 44 remains generally white and color-free to convey cleanliness to the user in the pudendal region. However, the random pattern 46 disguises those portions of the top sheet 32 and back sheet 34 that are most likely seen outside the undergarment 14. Thus, the random pattern 46 reduces the visibility and conspicuousness of the product 10 while also conveying cleanliness and comfort to the user.

Figure 3:
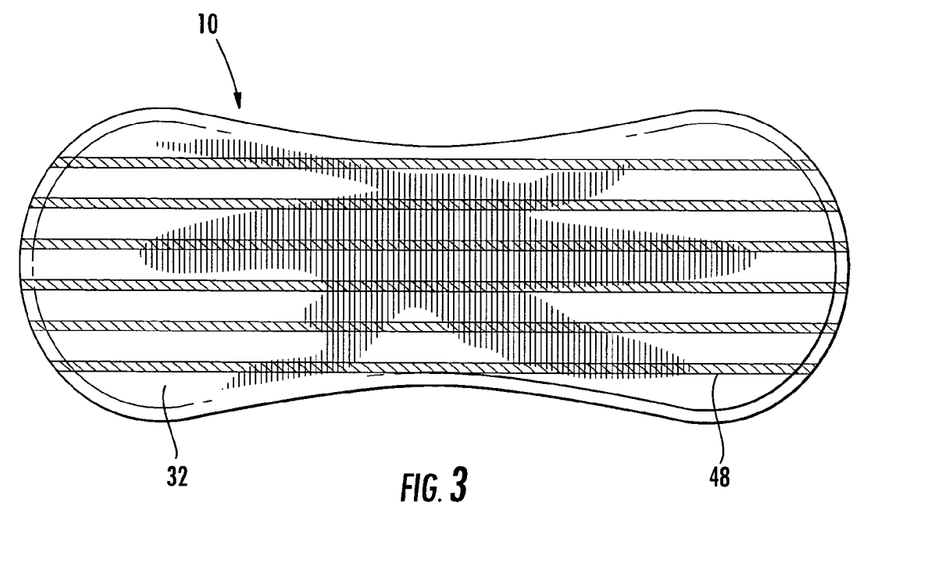
FIG. 3 is a top plan view of an alternate embodiment of the present invention.

FIG. 3 illustrates an embodiment having a repeating geometric pattern 48 on the top sheet 32. As shown, the geometric pattern 48 comprises generally parallel lines along the length of the top sheet 32, although other geometric shapes such as curves, arcs, and polygons are within the scope of this embodiment. In addition to disguising the product 10 to match the undergarment 14, the geometric pattern 48 may also provide the user with a convenient reference for properly positioning the product 10 radially and axially in the crotch of the undergarment 14.

Figure 4:
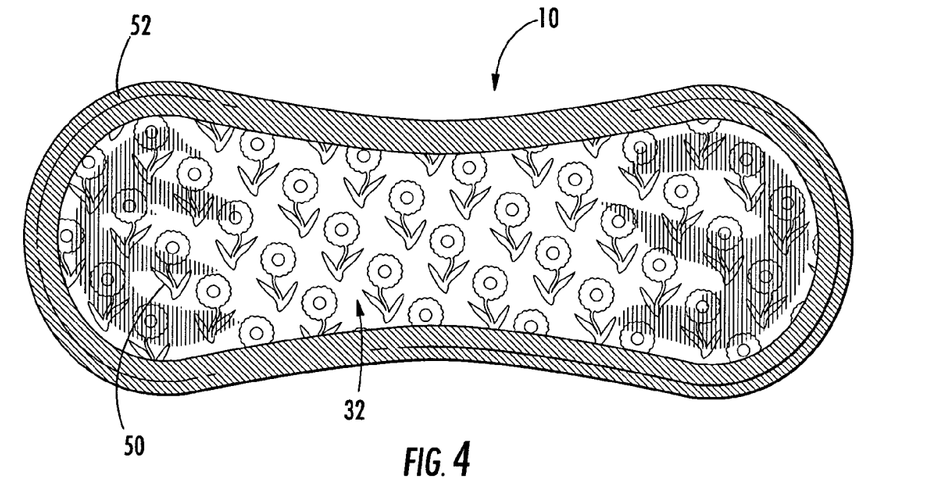
FIG. 4 is a top plan view of an alternate embodiment of the present invention.

FIG. 4 illustrates an embodiment that combines a repeating floral pattern 50 with a solid pattern 52. As before, the floral pattern 50 on the top sheet 32 matches the design 12 on the undergarment 14, disguising the personal care product 10 to blend in with the background of the undergarment 14. The solid pattern 52 around the periphery of the top sheet 32 may create a visual illusion of a structural border around the product 10. This visual allusion may provide additional comfort to the user by creating a sense of additional protection against leakage.

Figure 5:
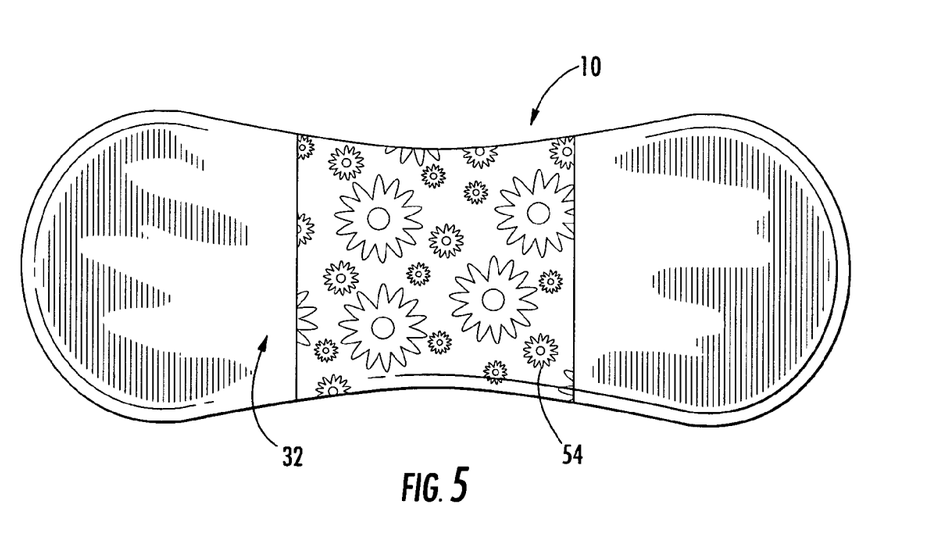
FIG. 5 is a top plan view of an alternate embodiment of the present invention.

FIG. 5 illustrates a randomly repeating pattern 54 in the portion of the top sheet 32 most likely to receive body exudates. The randomly repeating pattern 54 may hide or obscure any discoloration caused by additives or exudates. Alternately, the randomly repeating pattern 54 may highlight or signal the presence of exudates on the top sheet 32 to indicate a soiled product 10 to the user.

Figure 6A:
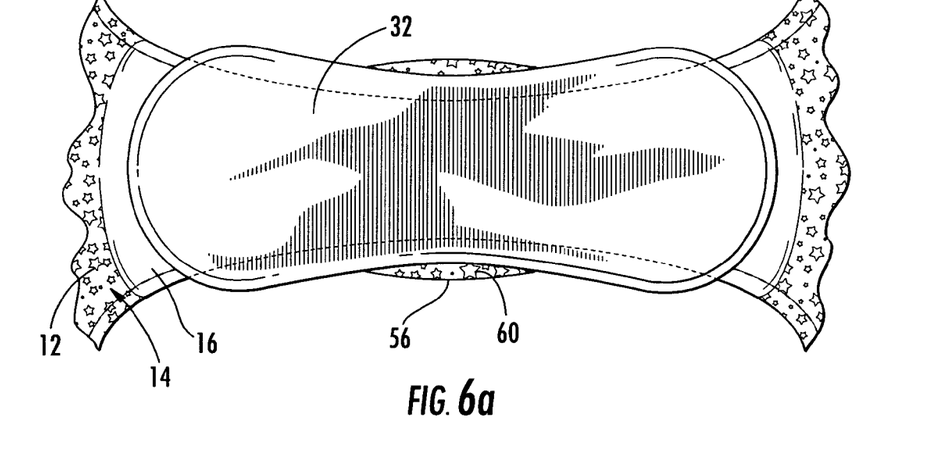
FIG. 6*a* is a top plan view of an alternate embodiment of the present invention.
Figure 6B:
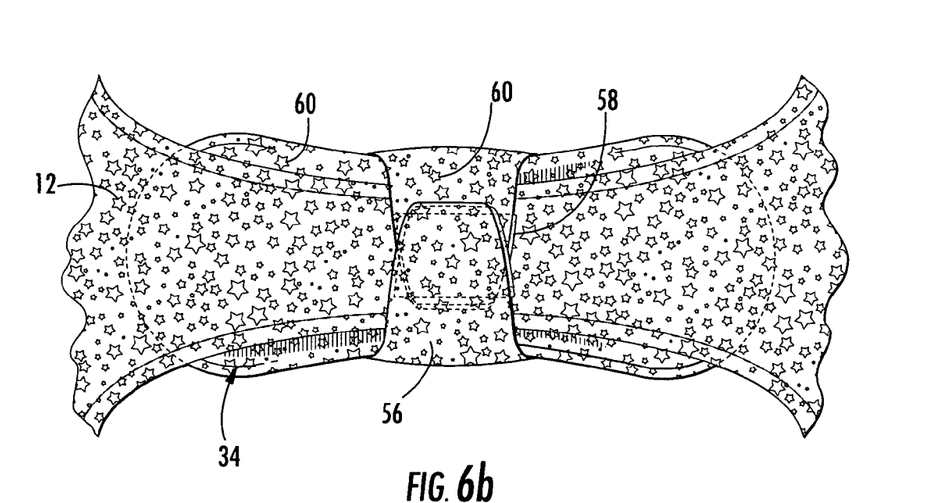
FIG. 6*b* is a bottom plan view of an alternate embodiment of the present invention.

FIGS. 6a and 6b provide top and bottom plan views, respectively, of an alternate embodiment from inside and outside the undergarment 14. In this embodiment, the personal care product 10 includes side flaps, wings, or tabs 56 that extend beyond the undergarment 14 to provide additional lateral coverage to the crotch 16 of the undergarment 14. The tabs 56 may include adhesive 58 to securely attach the tabs 56 to each other and/or the outside of the undergarment 14.

As shown in FIG. 6a, the tabs 56 may include a pattern 60 that matches the design 12 on the undergarment 14; however the top sheet 32 may remain essentially white to match the white crotch 16 of the undergarment 14. Viewing the embodiment from outside the undergarment 14, as shown in FIG. 6b, the portions of the back sheet 34 that are visible from outside the undergarment 14 may also include the pattern 60. In this embodiment, the top sheet 32 blends into the background of the generally white crotch 16 of the undergarment 14 while the tabs 56 and visible portions of the back sheet 34 blend into the background of the outside of the undergarment 14.

It should be understood by one of ordinary skill in the art that for each embodiment illustrated in the figures the respective pattern matches or complements the particular design on the undergarment. The particular pattern may be applied to the absorbent side or non-absorbent side the exterior layer, as long as the pattern remains generally visible. Moreover, the pattern may cover some or all of the exterior layer or parts thereof. For example, the pattern may exist on some or all of the top sheet, back sheet, and or tabs. Methods of applying the pattern to the exterior layer include printing, embossing, or any other method known in the art.

It should be appreciated by those skilled in the art that modifications and variations can be made to the embodiments of the invention set forth herein without departing from the scope and spirit of the invention as set forth in the appended claims and their equivalents.

What is claimed:

1. A system for disguising use of a personal care product, comprising:
    a. an undergarment having a design of outwardly visible characteristics of at least two selected from the group consisting of non-white colors, shapes, and designs;
    b. a personal care product designed to be placed at least partially within said undergarment, said personal care product comprising an absorbent material within an exterior layer, said exterior layer comprising a top sheet and a back sheet;
    c. a pattern defined on at least a portion of one of said top sheet or said back sheet, said pattern substantially matching said undergarment design such that upon placement of said personal care product in said undergarment, visible lines of distinction between said personal care product and said undergarment are disguised at areas of said personal care product containing said pattern.

2. The system as in claim 1, wherein said pattern further comprises any combination of geometric shapes, non-geometric shapes, repeating shapes, and non-repeating shapes.

3. The system as in claim 1, wherein said pattern is defined on said top sheet.

4. The system as in claim 3, wherein said pattern is defined substantially entirely over said top sheet.

5. The system as in claim 1, wherein said pattern is defined along opposite lateral sides of a longitudinal strip of said top sheet that does not include said pattern.

6. The system as in claim 1, wherein said pattern is defined on said back sheet.

7. The system as in claim 6, wherein said pattern is defined on substantially only portions of said back sheet that are outwardly visible when said personal care product is placed within said undergarment.

8. The system as in claim 6, wherein said pattern is defined substantially entirely over said back sheet.

9. The system as in claim 1, wherein said personal care product further comprises laterally extending wings that fold around a crotch region of said undergarment, said pattern defined on said wings.

10. The system as in claim 1, wherein said pattern is embossed on said exterior layer.

11. The system as in claim 1, wherein said pattern is printed on said exterior layer.

12. The system as in claim 1, wherein said exterior layer further includes an absorbent side and a non-absorbent side and said pattern is defined on said absorbent side of said exterior layer.

13. A method for disguising the use of personal care products placed in a user's undergarment, comprising:
    a. selecting an undergarment having a design of outwardly visible characteristics of at least two selected from the group consisting of non-white colors, shapes, and designs;
    b. on at least one outwardly visible surface of a personal care product intended to be placed within the undergarment, defining a pattern that substantially matches the visible design of the undergarment; and
    c. placing the personal care product in the undergarment such that the pattern substantially aligns with and matches the undergarment design and visible lines of distinction between the personal care product and undergarment are disguised.

14. The method as in claim 13, comprising defining the pattern on surfaces of the personal care product that are visible to the user in use of the personal care product.

15. The method as in claim 13, comprising defining the pattern on surfaces of the personal care product that are outwardly visible when the undergarment and personal care product are worn by the user.

16. The method as in claim 13, comprising defining the pattern substantially over a top sheet of the personal care product.

17. The method as in claim 13, comprising defining the pattern substantially over a back sheet of the personal care product.

18. The method as in claim 13, comprising defining the pattern substantially over a top sheet and back sheet of the personal care product.

19. The method as in claim 13, comprising defining the pattern on the personal care product by one of an embossing and a printing technique.

20. A personal care product adapted for placement in an undergarment having a design of outwardly visible characteristics of at least two selected from the group consisting of non-white colors, shapes, and designs, comprising: a. an exterior layer, said exterior layer comprising a top sheet and a back sheet; b. a pattern defined on at least a portion of one of said top sheet or said back sheet, said pattern substantially matching the undergarment design such that upon placement of said personal care product in the undergarment, visible lines of distinction between said personal care product and the undergarment are disguised at areas of said personal care product containing said pattern.

21. The product as in claim 20, wherein said pattern comprises any combination of geometric shapes, non-geometric shapes, repeating shapes, and non-repeating shapes.

22. The product as in claim 20, wherein said pattern is defined on said top sheet.

23. The product as in claim 22, wherein said pattern is defined substantially entirely over said top sheet.

24. The product as in claim 20, wherein said pattern is defined along opposite lateral sides of an un-patterned longitudinal strip of said top sheet.

25. The product as in claim 20, wherein said pattern is defined on said back sheet.

26. The product as in claim 25, wherein said pattern is defined on substantially only portions of said back sheet that are outwardly visible when said personal care product is placed within said undergarment.

27. The product as in claim 25, wherein said pattern is defined substantially entirely over said back sheet.

28. The product as in claim 20, further comprising laterally extending wings that fold around a crotch region of the undergarment, said pattern defined on said wings.

29. The system as in claim 20, wherein said exterior layer further includes an absorbent side and a non-absorbent side and said pattern is defined on said absorbent side of said exterior layer.

* * * * *